United States Patent
Dalle Carbonare et al.

(10) Patent No.: US 8,147,811 B1
(45) Date of Patent: Apr. 3, 2012

(54) USE OF HYALURONIC ACID DERIVATIVES IN PHARMACEUTICAL PREPARATIONS AND BIOMATERIALS FOR THE PREVENTION AND TREATMENT OF CUTANEOUS SCARS

(75) Inventors: Maurizio Dalle Carbonare, Padua (IT); Lanfranco Callegaro, Thiene Vicenza (IT)

(73) Assignee: Fidia Farmaceutici S.p.A., Abano Terme (IT)

(*) Notice: Subject to any disclaimer, the term of this patent is extended or adjusted under 35 U.S.C. 154(b) by 1302 days.

(21) Appl. No.: 10/019,387

(22) PCT Filed: Jun. 29, 2000

(86) PCT No.: PCT/EP00/06087
§ 371 (c)(1),
(2), (4) Date: Mar. 26, 2003

(87) PCT Pub. No.: WO01/00190
PCT Pub. Date: Jan. 4, 2001

(30) Foreign Application Priority Data

Jun. 29, 1999 (IT) .................................. PD99A0144

(51) Int. Cl.
*A61K 8/18* (2006.01)
(52) U.S. Cl. ...................................... 424/70.1; 424/443
(58) Field of Classification Search .................. 424/70, 424/443
See application file for complete search history.

(56) References Cited

U.S. PATENT DOCUMENTS

| 4,851,521 A | * | 7/1989 | della Valle et al. | 536/55.1 |
| 5,658,331 A | * | 8/1997 | Della Valle et al. | 128/898 |
| 5,676,964 A | * | 10/1997 | Della Valle et al. | 424/423 |
| 5,824,335 A | * | 10/1998 | Dorigatti et al. | 424/443 |
| 5,939,323 A | * | 8/1999 | Valentini et al. | 435/395 |

FOREIGN PATENT DOCUMENTS

| WO | WO94/17837 | * | 8/1994 |
| WO | WO 97/07833 | | 3/1997 |
| WO | WO 9707833 | * | 3/1997 |
| WO | WO9707833 | * | 3/1997 |
| WO | WO99/04828 | * | 2/1999 |
| WO | WO 99/04828 | * | 2/1999 |

OTHER PUBLICATIONS

WO 97/07833, Fidia Advanced Biopolymers, Mar. 6, 1997.*
WO 99/04828, Fidia Advanced, Feb. 4, 1999.*
WO 94/17837, Fidia Advanced Biopolymers, Aug. 18, 1994.*
Jeffrey et al. (Ckinical Materials (1991)171-177.*
Biomaterials 17 1996.*
Davidson, J.M. et al., "Hyaluronate derivatives and their application to wound healing: preliminary observations" Clinical Materials, vol. 8, No. 1-2 (1991) pp. 171-177.

(Continued)

Primary Examiner — Gollamudi Kishore
Assistant Examiner — Snigdha Maewall
(74) Attorney, Agent, or Firm — Birch, Stewart, Koalsch & Birch, LLP

(57) ABSTRACT

Use of hyaluronic acid derivatives for the preparation of biomaterials for the prevention of the formation and the treatment of cutaneous scars, wherein the hyaluronic acid derivatives are optionally combined with pharmacologically or biologically active compounds.

7 Claims, 1 Drawing Sheet

OTHER PUBLICATIONS

Ruiz-Cardona, L. et al., "Application of benzyl hyaluronate membranes as potential wound dressings: evaluation of water vapour and gas permeabilities" Biomaterials, GB, Elsevier Science Publishers BV., Barking, vol. 17, No. 16, Aug. 1, 1996, pp. 1639-1643.

Alberts, Bruce et al., Molecular Biology of the Cell, 2nd Edition, pp. 24 and 25, (1989).

De Iaco, Pier Andrea et al., "Efficacy of a hyaluronan derivative gel . . . ," Surgery, vol. 130, No. 1, pp. 60-64, (2001).

Belluco, Claudio et al., "Prevention of Postsurgical Adhesions with an Autocrosslinked . . . ," Journal of Surgical Research, (2001), 100, pp. 217-221.

Wyngaarden, James B. et al., Cecil Textbook of Medicine, 18th Edition, (1998), p. 2306.

Bettinger, David A. et al., "Hyaluronic Acid Impedes Reepithelization . . . ," Journal of Burn Care & Rehabilitation, Jul./Aug. 1996, pp. 302-304.

* cited by examiner

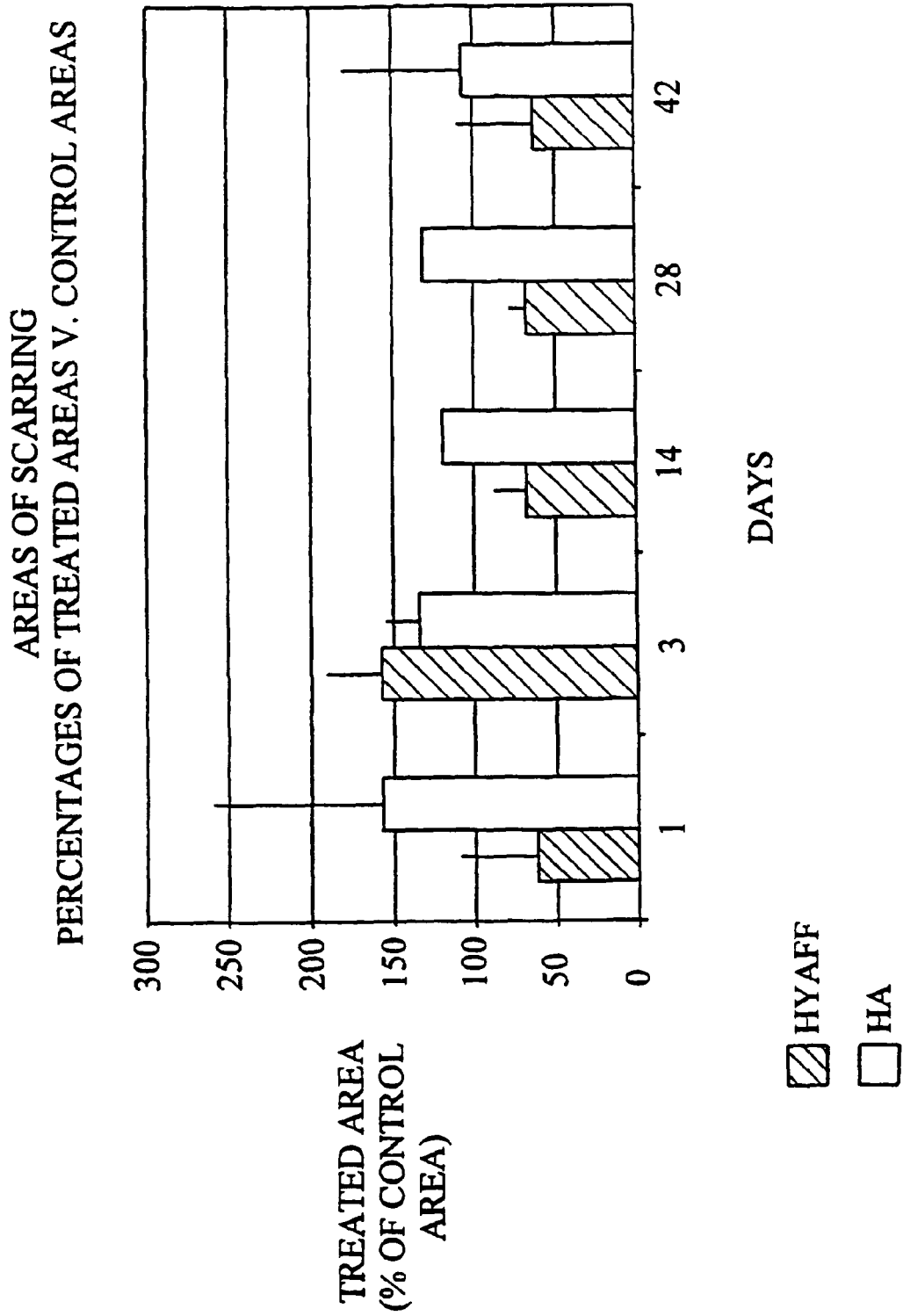

USE OF HYALURONIC ACID DERIVATIVES IN PHARMACEUTICAL PREPARATIONS AND BIOMATERIALS FOR THE PREVENTION AND TREATMENT OF CUTANEOUS SCARS

This application is the national phase under 35 U.S.C. §371 of PCT International Application No. PCT/EP00/06087 which has an International filing date of Jun. 29, 2000, which designated the United States of America and was published in English.

SUBJECT OF THE INVENTION

The present invention is directed to the use of hyaluronic acid derivatives for the preparation of biomaterials for the prevention of the formation and the treatment of cutaneous scars, wherein the hyaluronic acid derivatives are optionally combined with additional pharmacologically or biologically active compounds.

BACKGROUND OF THE INVENTION

A cutaneous scar is the outcome of the repair processes that restore the continuity of damaged skin. Normally, this repair process leads to the formation of new tissue with a visibly different appearance from the surrounding skin. In particular, scar tissue may lack pigmentation, or have too much, or be depressed, shiny, rough, normotrophic, retracted or lacking in elasticity. At a microscopic level, scar tissue is characterized by an abundant and disorganized deposit of collagen arranged in thick, dense, twisted bundles. The scarring process is very lengthy, as the reshaping phase remains active for years. In some cases, during the initial reshaping phase, the scarring process may become pathological, giving rise to hypertrophic scars or keloids. Hypertrophic scars are characterized by excessive thickening, but without any spreading beyond the wound area. Conversely, in the case of keloids, besides the thickening of the newly formed tissue, there is colonization of the surrounding area too. The formation of both hypertrophic scars and keloids seems to involve an imbalance of immune system. From a histological point of view, they are both characterized by a moderate amount of cell infiltration and by an excessive and disorganized deposit of thick bundles of collagen. Scars may cause functional difficulties and are unsightly. The chief functional difficulties occur when the scar forms on critical areas of skin such as at the joints. In this case, the poor elasticity of scar tissue may lead to incorrect functioning of the joint itself.

Normal wound healing in response to tissue injury involves several integrated processes: inflammation, production of granulation tissue, formation of the extracellular matrix, wound contraction, and, finally, scar formation. In the final phases of wound healing, fibroblasts degrade and produce bundles of collagen fibers. These bundles become thicker and are aligned along the lines of tension to which the tissues are exposed. As a result of these changes, wound tensile strength gradually increases. The resulting scar is relatively acellular and has fewer macrophages, blood vessels, and fibroblasts than the unwounded tissue.

Scars may be normotrophic, atrophic, hypertrophic, or keloidal. Both hypertrophic and keloidal scars are abnormal responses to tissue injury. Hypertrophic scars mature and flatten over time, usually after 6 months. The keloid appears as a shiny, smooth, raised proliferation of scar tissue with typical crablike extensions beyond the site of the original injury Keloids differ from hypertrophic scars in that their development is delayed, sometimes occurring months after tissue injury. Keloids do not regress, and they frequently cause pain, itching, and burning. Keloids are more common in African Americans, Hispanics, and persons with a personal or family history of keloids.

In atrophic scars, there is thinning of the skin and loss of normal architecture. Striae distensae, a so-called stretch mark, is a common dermal atrophic scar that tends to appear during periods of rapid weight gain and in the presence of excess glucocorticoid, as well as late in gestation.

Treatment with intralesional steroids, 10 to 40 mg/ml once a month for up to 6 months, can effectively flatten keloid and hypertrophic scars. Cryotherapy (a 30-second application once a month for 3 months) has been found to be safe and effective. Topical silicone gel sheeting, which was first used for burn scars, has been used in the treatment of keloids and hypertrophic scars. There is no release of silicone into the skin, and there are no adverse side effects from this treatment. The mechanism of action is unknown. Potential side effects of intralesional corticosteroid treatment include atrophy, depigmentation, telangiectasia, and ulceration and dose-related systemic effects.

Keloids are proliferative dermal growths that develop after skin injury. Unlike hypertrophic scars, the scar tissue extends beyond the borders of the original wound. The first description of keloids was offered in the Smyth papyrus on surgical techniques in Egypt 1700 BC. Subsequently, Alibert in 1806 used the term "cheloide", derived from the Greek "chele" or crab claw to describe the lateral growth of tissue into normal skin. In addition to the cosmetic disfigurement these scars represent to affected patients, they can be pruritic, tender and can be complicated by secondary infections.

Keloids occur most commonly between the ages of 10 and 30 years. Deeply pigmented people are more susceptible to proliferative scarring than those with fair skin. Keloid formation correlates with sites where melanocyte concentrations are greatest. In addition, pregnancy and puberty, times of increased physiologic pituitary activity, have been associated with increased keloid formation. Incidence has been reported at 4.5 and 16% in black and Hispanic populations respectively. Definitive incidence figures are not known for hypertrophic scars. Inheritance patterns of keloids are autosomal dominant and autosomal recessive and they have been genetically associated with HLA B14, B21, Bw16, Bw35, DR5, and DQw3.

Keloids differ from hypertrophic scars clinically and histologically. Clinically, keloids are a deep red or purple color with raised indurated tissue that extends beyond the original wound borders. Hypertrophic scars have a less impressive white or pink color, with firm tissue limited to original wound border. Histologically, keloids are composed of disorganized thick hyalinized collagen with a prominent mucoid matrix, whereas hypertrophic scars are characterized by fewer, more organized collagen fibers with a scanty mucoid matrix. The fibroblast concentration is more prominent in hypertrophic scars. Hypertrophic and keloidal scarring is more common in darkly pigmented races. There is increased proliferative scarring during increased hormonal stimulation. Keloids are characterized by more disorganized, thickened collagen fibers and a prominent mucoid matrix.

Moreover, the aesthetic problems due to scar formation must not be underestimated, as scarring often causes psychological disorders, especially when it affects the face.

The methods used to date to make scars less visible are of a surgical nature, such as the technique using expanded strips of skin. This technique involves the expansion of areas of skin by subcutaneous agents. Once a sufficient amount of skin has been obtained to cover the scarred area, the scar is surgically removed and the expanded skin is grafted into place.

To date, there have been no efficacious pharmacological therapies to cure normotrophic scarring, pathological scarring can be treated pharmacologically using cortisone derivatives and, in some cases, strong immunosuppressors such as cyclosporin. In order to improve the elasticity of the scar tissue and induce its reabsorption, softening compositions are used such as creams and adhesive silicon films for prolonged application. Besides said topical treatments, patients undergo therapies with instruments designed to massage the scarred area by aspiration, to re-establish its elasticity and softness. Said remedies, however, have various disadvantages such as the need to perform one or more operations on the patient and, in the case of pharmacological therapy, their limitation to the treatment of pathological scarring and their unproven efficacy. Lastly, the products for topical use and therapeutic practices give fairly good results with regard to functionality, but poor aesthetic results.

It is well known that daily administration of hyaluronic acid can lead to scar-free tissue repair in a foetal animal model and that this glycosaminoglycan plays an important role in skin reconstruction. Moreover, technical experience has taught us that long-term high quantities of hyaluronic acid create one of the fundamental conditions to obtain scar-free skin repair (West D. C. et al., J. Biochem. Cell Biol. 1997, 29, 201-210, Iocono J. A., J. Pediatric Surg. 1998, 33, 564-567).

Hyaluronic acid is a polysaccharide ether composed of alternating residues of D-glucuronic acid and N-acetyl-D-glycosamine. It is a straight-chain polymer with a molecular weight which may vary between 50,000 and 13,000,000 Da, according to the source from which it was obtained and the methods of preparation which were used. It is present in nature in the pericellular gels, in the fundamental substance of the connective tissue of vertebrae organisms of which it represents one of the main components, in the synovial fluid of joints, in the vitreous humor, in the tissues of human umbilical cord and in rooster combs.

In recent years, various types of hyaluronic derivatives have been synthesized to obtain compounds with pharmacological properties or which can be processed in various forms of biodegradable and biocompatible biomaterials for use in the various fields of medicine, surgery and tissue engineering.

For example, the total or partial esters of hyaluronic acid and the autocross-linked derivatives of hyaluronic acid are known, as is their use in the pharmaceutical, cosmetic field an in that of biodegradable materials (U.S. Pat. Nos. 4,851,521; 4,965,353; 5,676,964).

Moreover, hyaluronic acid derivatives have new properties which starting hyaluronic acid does not have, due to the insertion of specific molecules in their structure. For example, the sulphated derivatives of hyaluronic acid present anticoagulant properties and are resistant to hyaluronidase (WO 95/25751, WO 98/45335).

Lastly, the use of N-sulphated derivatives in the prevention of pathological scarring such as hypertrophic scarring and keloids is known. However, said derivatives have never been reported as being able to prevent the formation of normotrophic scarring.

It has now been found, surprisingly, that hyaluronic acid derivatives are efficacious in reducing the extent of normotrophic scarring and that said activity is greater than that of hyaluronic acid itself.

DETAILED DESCRIPTION OF THE INVENTION

The aim of the present invention is to provide biomaterials containing at least one hyaluronic acid derivative which is efficacious in reducing the area of skin affected by scarring. The hyaluronic acid derivatives may be used in combination, with one or more pharmacologically or biologically active compounds.

For the preparation of the various hyaluronic acid derivatives used in the present invention, it is possible to use hyaluronic acids of any origin, such as for example the acids extracted from the above mentioned natural starting materials, for example from cocks' combs. The preparation of such acids is described in literature: preferably, purified hyaluronic acids are used. According to the invention, especially used are hyaluronic acids comprising molecular fractions of the integral acids obtained directly by extraction of the organic materials with molecular weights varying within a wide range, for example, from about 90%-80% (MW=11.7-10.4 million) to 0.2% (MW=30,000) of the molecular weight of the integral acid having a molecular weight of 13 million, preferably between 5% and 0.2%. Such fractions may be obtained with various procedures described in literature, such as by hydrolyzing, oxidizing, enzymatic or physical procedures, such as mechanical or radiational procedures. Primordial extracts are therefore often formed during these same purification procedures (for example see the article by Balazs et al. quoted above in "Cosmetics & Toiletries"). The separation and purification of the molecular fractions obtained are brought about by known techniques, for example by molecular filtration.

One fraction of purified HY suitable for use according to the invention is for example that known as "non-inflammatory-NIF-NaHA sodium hyaluronate described by Balazs in the booklet "Healon"—A guide to its use in Ophthalmic Surgery, D. Miller & R. Stegmann, eds. John Wiley & Sons, NY 81983, p. 5.

Particularly important as starting materials for the derivatives used in the present invention are two purified fractions obtainable from hyaluronic acid, for example the ones extracted from cocks' combs, known as "Hyalastine" and "Hyalectin". The fraction Hyalastine has an average molecular weight of about 50,000 to 100,000 while the fraction Hyalectin has an average molecular weight of between about 500,000 and 730,000. A combined fraction of these two fractions has also been isolated and characterized as having an average molecular weight of about 250,000 to about 350,000. This combined fraction may be obtained with a yield of 80% of total hyaluronic acid available in the particular starting material, while the fraction Hyalectin may be obtained with a yield of 30% and the fraction Hyalastine with a yield of 50% of the starting HY. The preparation of these fractions and uses in making the derivatives as described in EP 0216453 B1.

The salification of HY with the above metals, for the preparation of starting salts for the particular esterification procedure of the present invention described above, is performed in a per se known manner, for example by reacting HY with the calculated based quantity, for example with alkaline hydrates or with basic salts of such metals such as carbonates or bicarbonates.

Of the hyaluronic acid derivatives that can be used in the preparation of the biomaterials according to the present invention, the following are to be preferred:
(1) The esters of hyaluronic acid wherein part or all of the carboxy functions are esterified with alcohols of the aliphatic, aromatic, arylaliphatic, cycloaliphatic, heterocyclic series (EP 0 216 453 B1);
(2) The autocross-linked esters of hyaluronic acid wherein part or all of the carboxy groups are esterified with the alcoholic functions of the same polysaccharide chain or of other chains (EP 0 341 745 B1);

(3) The cross-linked compounds of hyaluronic acid wherein part of all of the carboxy groups are esterified with polyalcohols of the aliphatic, aromatic, arylaliphatic, cycloaliphatic, heterocyclic series, generating cross-linking by means of spacer chains (EP 0 265 116 B1);

(4) The hemiesters of succinic acid or the heavy metal salts of the hemiester of succinic acid with hyaluronic acid or with partial or total esters of hyaluronic acid (WO 96/357201);

(5) The O-sulphated derivatives (WO 95/25751) or O/N-sulphated derivatives (WO 98/45335);

(6) The amidic derivatives of hyaluronic acid or of the above-listed compounds.

1. Esters of Hyaluronic Acid with Alcohols

The hyaluronic acid derivatives can be total or partial esters with alcohols of the aliphatic, aromatic, arylaliphatic, cycloaliphatic or heterocyclic esters. Alcohols of the aliphatic series to be used as esterifying components of the carboxylic groups of hyaluronic acid are for example those with a maximum of 34 carbon atoms, which may be saturated or unsaturated and which may possibly also be substituted by other free functional or functionally modified groups, such as amine, hydroxyl, aldehyde, ketone, mercaptan, or carboxyl groups or by groups derived from these, such as hydrocarbyl or di-hydrocarbylamine groups (from now on the term "hydrocarbyl" will be used to refer not only to monovalent radicals of hydrocarbons such as the $C_nH_{2n+1}$ type, but also bivalent or trivalent radicals, such as "alkylenes" $C_nH_{2n}$ or "alkylidenes" $C_nH_{2n}$), ether or ester groups, acetal or ketal groups, thioether or thioester groups, and esterified carboxyl or carbamide groups and carbamide substituted by one or more hydrocarbyl groups, by nitrile groups or by halogens.

Of the above mentioned groups containing hydrocarbyl radicals, these are preferably lower aliphatic radicals, such as alkyls, with a maximum of 6 carbon atoms. Such alcohols may also be interrupted in the carbon atom chain by heteroatoms, such as oxygen, nitrogen and sulfur atoms. Preferred are alcohols substituted with one or two of the said functional groups.

Alcohols of the above mentioned group which are preferably to be used are those with a maximum of 12, and especially 6 carbon atoms, and in which the hydrocarbyl atoms in the above mentioned amine, ether, ester, thioether, thioester, acetal, ketal group represent alkyl groups with a maximum of 4 carbon atom, and also in the esterified carboxyl or substituted carbamide groups the hydrocarbyl groups are alkyls with the same number of carbon atoms, and in which in the amine of carbamide groups may be alkylenamine or alkylencarbamide groups with a maximum of 8 carbon atoms. Of these alcohols special mention should be given to those which are saturated and not substituted such as the methyl, ethyl, propyl, and isopropyl alcohols, normal butyl alcohol, isobutyl alcohol, tertiary butyl alcohol, the amyl, pentyl, hexyl, octyl, nonyl and dodecyl alcohols and, above all, those with a linear chain, such as normal octyl and dodecyl alcohols. Of the substituted alcohols of this group, the bivalent alcohols should be listed, such as ethyleneglycol, propyleneglycol and butyleneglycol, the trivalent alcohols such as glycerine, the aldehyde alcohols such as tartronic alcohol, the carboxylic alcohols such as lactic acids, for example, glycolic acid, malic acid, the tartaric acids, citric acid the aminoalcohols, such as normal aminoethanol, aminopropanol, normal aminobutanol and their dimethylated and diethylated derivatives in the amine function, choline, pyrrolidinylethanol, piperidinylethanol, piperazineylethanol and the corresponding derivatives of normal propyl or normal butyl alcohol, monothioethyleneglycol or its alkyl derivatives, such as the ethyl derivative in the mercaptan function.

Of the higher saturated aliphatic alcohols the following should be mentioned: cetyl alcohol and myricyl alcohol, but the higher unsaturated alcohols with one or two double bonds, are especially important, such as especially those contained in many essential oils and with affinity to terpene, such as citronellol, geraniol, nerol, nerolidol, linalool, farnesol phytol. Of the unsaturated lower alcohols it is necessary to consider allyl alcohol and propargyl alcohol. Of the araliphatic alcohols special attention should be given to those with only one benzene residue and in which the aliphatic chain has a maximum of 4 carbon atoms, which the benzene residue can be substituted by between 1 and 3 methyl or hydroxyl groups or by halogen atoms, especially by chlorine, bromine and iodine, and in which the aliphatic chain may be substituted by one or more functions chosen from the group containing fee amine groups or mono- or dimethylated or by pyrrolidine or piperidine groups. Of these alcohols special attention should be given to benzyl alcohol and phenyl alcohol.

The degree of esterification of hyaluronic acid with the above mentioned alcohols can be varied. Normally, a high degree of esterification up to total esterification of hyaluronic acid increases its lipophilic character and therefore lessens its solubility in water.

Of particular interest however are those partial esters in which at lest 5% and at most 90% of all the carboxylic groups of HY are esterified, and especially those with an esterified percentage of between 50 and 80%, most especially those of 65 to 80% esterification.

In the partial esters, the non-esterified carboxylic groups may be kept free or may be salified. It is possible to form inorganic salts deriving from alkaline metals, such as potassium and especially sodium and ammonium, or deriving from alkaline earth metals, such as calcium, or magnesium or aluminum salts. Particularly interesting are the salts with organic bases, especially nitrogenized bases and therefore aliphatic, arylaliphatic, cycloaliphatic or heterocyclic amines.

These ammonic salts may derive from therapeutically acceptable but inactive amines or from amines with therapeutic action. Of the former the aliphatic amine above all should be considered, such as mono- di- and tri-alkylamines with alkyl groups having a maximum of 18 carbon atoms or arylalkylamines with the same number of carbon atoms in the aliphatic part and where aryl means a benzene group possible substituted by 1 and 3 methyl groups or halogen or atoms of hydroxyl groups. The biologically inactive bases for the formation of salts may also be cyclic such as monocyclic alkylenamines with cycles of between 4 and 6 carbon atoms, possibly interrupted in the cycle of heteroatoms chosen from the group by nitrogen, oxygen and sulfur, such as piperidine or morpholine, and may be substituted for example by aminic or hydroxylic functions, such as aminoethanol, ethylendiamine, ephedrine or choline.

It is also possible to form the quaternary ammonium salts of the partial esters, for example the salts of tetraalkylammonium with the above mentioned number of carbon atoms and preferably salts of such a type in which the fourth alkyl group has between 1 and 4 carbon atoms, for example a methyl group.

Among the biologically active amine whose therapeutic actions may be put to use, are included all the nitrogenized and basic drugs such as those included in the following groups:

alkaloids, peptides, phenothiazines, benzodiazepines, thioxanthenes, hormones, vitamins anticonvulsants, antipsychotics, antiemetics, anesthetics, hypnotics, anorexics, tranquilizers, muscle relaxants, coronary vasodilators, antineoplastics, antibiotics, antibacterials, antivirals, antimalarials, carbonic anhydrase inhibitors, non-steroid anti-inflammatory agents, vasoconstrictors, cholinergic agonists, cholinergic antagonists, adrenergic agonists, adrenergic antagonists, narcotic antagonists.

Method of Preparing HY Esters

Method A:

The esters of hyaluronic acid according to the invention may be prepared by methods known per se for the esterification of carboxylic acids, for example by treatment of free hyaluronic acid with the desired alcohols in the presence of catalyzing substances, such as strong inorganic acids or ionic exchanges of the acid type, or with an etherifying agent capable of introducing the desired alcoholic residue in the presence of inorganic or organic bases. As etherifying agents it is possible to use those known in literature, such as especially the esters of various inorganic acids or of organic sulphonic acids, such as hydracids, that is hydrocarbyl halogenides, such as methyl or ethyl iodide, or neutral sulphates or hydrocarbyl acids, alfites, carbonates, silicates, phosphites or hydrocarbyl sulfonates, such as methyl benzene or p-toluenesulfonate or methyl or ethyl chlorosulfonate. The reaction may take place in a suitable solvent, for example an alcohol, preferably that corresponding to the alkyl group to be introduced in the carboxyl group. But the reaction may also take place in on-polar solvents, such as ketones, ethers, such as dioxane or aprotic solvents, such as dimethylsulphoxide. As a base it is possible to use for example a hydrate of an alkaline or alkaline earth metal or magnesium or silver oxide or a basic salt or one of these metals, such as a carbonate, and, of the organic bases, a tertiary azotized base, such as pyridine or collidine. In the place of the base it is also possible to use an ionic exchanger of the basic type.

Another esterification method employs the metal salts or salts with organic azotized bases, for example ammonium or ammonium substitute salts. Preferable, the salts of the alkaline or alkaline earth metals are used, but also any other metallic salt may be used. The esterifying agents are also in this case those mentioned above and the same applies to the solvents. It is preferable to use aprotic solvents, for example dimenthysulphoxide and dimethylformamide.

In the esters obtained according to this procedure or according to the other procedure described hereafter, free carboxylic groups of the partial esters may be salified, if desired, in a per se known manner.

Method B:

They hyaluronic esters of the present invention may, however, be prepared to advantage by the method described in EP 0216453 B1. This method consists of treating a quaternary ammonium salt of an acidic polysaccharide containing carboxyl groups with an etherifying agent, preferably in an aprotic organic solvent.

2. Autocross-Linked Esters of Hyaluronic Acid

Also useful in the invention are so called "autocrosslinked" esters of hyaluronic acid which are cross-linked hyaluronic acid products wherein the first portion of 1-100%, preferably 5-95%, more preferably 10-75%, 25-75%, or 25-50%, of the carboxyl groups of said hyaluronic acid are cross-linked by ester bonding or lactonic bonding to hydroxyl groups of the same hyaluronic acid molecule and/or to hydroxyl groups of different hyaluronic acid molecules; and a second portion of carboxyl groups, if present, of said hyaluronic acid are either salified, or are esterified with aliphatic, araliphatic, cycloaliphatic or heterocyclic alcohols. Said alcohols of the aliphatic series have a maximum of 34 carbon atoms and may be substituted by one or two functional groups chosen from the group formed by amino, hydroxy, mercapto, aldehydro, ketal, carboxy, hydrocarbyl, and dihydrocarbylamino, ether, ester, thioester, acetal, ketal, carbamidic groups or carbamidic groups substituted by one or more alkyl groups, the hycrocarbyl radicals in these groups having a maximum of 6 functionally modified carbon atoms, and in which alcohols of the aliphatic series may be interrupted in the carbon atom chain by heteroatoms chosen from the group formed by oxygen, sulfur and nitrogen. Said alcohols of the aralipathic series have only one benzene residue and have an aliphatic chain with a maximum of 4 carbon atoms and wherein the benzene residue may be substituted by between 1 and 3 methyl or hydroxy groups, by halogen atoms, and wherein the aliphatic chain may be substituted by one or two functions chosen from the group consisting of free amino groups or mono- or diethyl groups or by pyrrolidine or piperidine groups. Said alcohols of the cycloaliphatic or aliphatic-cycloaliphatic series are mono- or polycyclic hydrocarbons with a maximum of 34 carbon atoms. Said heterocyclic alcohols are mono- or polycyclic cycloaliphatic or aliphatic cycloaliphatic alcohols interrupted in their carbon atom chain or ring by one or more heteroatoms chosen from the group formed by nitrogen, oxygen and sulfur. The alcohols of the cycloaliphatic or aliphatic cycloaliphatic series may be derived from mono or polycyclic carbohydrates, and have a maximum of 34 carbon atoms, and may be unsubstituted and may contain one or more substitutents, mentioned above for the aliphatic alcohols, or the aliphatic-cycloaliphatic polycyclic alcohols, sterols, cholic acids and steroids, or wherein the heterocyclic alcohols are derivatives of the above-said cycloaliphatic or aliphatic-cycloaliphatic alcohols, wherein the linear or cyclic chains are interrupted by one to three hetero atoms chosen from the group formed by —O—, —S—, —N and —NH, as well as genins, digitoxigenin, gitoxigenin, digoxigenin, strophanthidin, tigogenin saponins and vitamin alcohols. The third portion of carboxyl groups, if present, is either salified or in form of the free acid.

These "inner" esters of hyaluronic acids, in which there is no intervention by OH groups of other alcohols, can also be defined as "auto-crosslinked hyaluronic", since the formation of a mono- or polymolecular cross-link is the consequence of the above-mentioned internal esterification. The adjective "cross-linked" refers to the crosswise connections between the carboxyls and hydroxyls of the hyaluronic molecules.

These inner esters can be total or partial, depending on whether all or only part of the carboxy functions are esterified in the above manner. In the partial inner esters, further carboxy functions can be either totally or partially esterified with monovalent or polyvalent alcohols, thus forming "external" ester groups, and in the partial esters of both these ester groups the non-esterified carboxy functions may be free or salified with metals or organic bases.

Esterification between different hyaluronic molecules consequently increases their molecular weight, which can be roughly doubled or multiplied according to the number of molecules involved in the crosslinking. The degree of "polymerization" varies according to the conditions used in the preparation procedure described hereafter, such as temperature, reaction duration, but it may likewise depend on the hyaluronic acid to be crosslinked. Even thought it is impossible to ascertain the ratio between the two types of ester bonds, an approximate representation can be made on the basis of the molecular weight, this being proportional to the number of molecules of the hyaluronic acid aggregate of the above-said bonds of intermolecular inner esters. Particularly important are the crosslinked products resulting from the fusion of two or three hyaluronic acid molecules, and products varying in their degree of "polymerization" in these terms. They can be obtained for example by means of the procedure described in EP 0 341 745 B1.

Hyaluronic acid containing carboxy functions which serve as the basic starting materials to the inner esters are all those already known and described in literature, such as the natural ones of animal or vegetable origin, and synthetic derivatives of the same.

In the inner esters, the carboxy groups still left intact can be salified with organic or inorganic bases. The choice of bases for the formation of such salts is based on the intended use of the product. The inorganic salts are preferably those of alkaline metals, such as sodium or potassium salts or ammonium salts, cesium salts, salts of alkaline earth metals, such as calcium, magnesium or aluminum.

The salts of organic bases are especially those of aliphatic, araliphatic, cycloaliphatic or heterocyclic amines. The ammonium salts of this type may derive from therapeutically acceptable, but inactive, amines, or from amines with a therapeutic action. Of the former, special consideration should be given to aliphatic amines, for example, mono, di and trialkylamines, with alkyl groups with a maximum of 18 carbon atoms, or arylakylamines with the same number of carbon atoms in the aliphatic part and where aryl means a benzene group possibly substituted by between 1 and 3 hydroxy groups. As therapeutically acceptable amines, but not active in themselves, cyclic amines are very suitable, such as alkylene amines with rings of between 4 and 6 carbon atoms, possibly interrupted in the ring by heteroatoms, such as oxygen, sulphur and nitrogen, such as piperidine, morpholine or piperazine, or may be substituted for example by amino or hydroxy functions, as in the case of aminoethanol, ethylene diamine or choline.

Of the higher aliphatic saturated alcohols, the following should be given as examples: cetyl alcohol and myricyl alcohol, but of special importance for the purposes of the present invention are the higher unsaturated alcohols with one or two double bonds, such as especially those contained in many essential oils and having affinity with terpenes, such as citronellol, geraniol, nerol, nerolidol, linalool, farnesol, phytol. Of the lower unsaturated alcohols, the ones to be considered are allyl alcohol and propargyl alcohol.

The araliphatic alcohols, are those with only one benzene residue and in which the aliphatic chain has a maximum of 4 carbon atoms and in which the benzene residue may be substituted by between 1 and 3 methyl or hydroxy groups or by halogen atoms, especially by chlorine, bromine, iodine, and in which the aliphatic chain may be substituted by one or more functions chosen from the groups comprising free amino groups or mono or dimethyl or diethyl groups or by pyrrolidine or piperidine groups. Of these alcohols special mention should be given to benzyl alcohol and phenethyl alcohol.

Alcohols of the cycloaliphatic or aliphatic cycloaliphatic series may derive from mono or polycyclic carbohydrates, and have a maximum of 34 carbon atoms, may be unsubstituted and may contain one or more substituents, such as those mentioned above for the aliphatic alcohols. Of the alcohols derived from single-ringed cyclic carbohydrates, special mention should be given to those with a maximum of 12 carbon atoms, the rings having preferably between 5 and 7 carbon atoms, which may be substituted for example by between one and three lower alkyl groups, such as methyl, ethyl, propyl, or isopropyl groups. As alcohols specific to this group, cyclohexaonl, cyclohexanediol, 1,2,3 cyclohexanetriol and 1,3,5 cyclohexanetriol (phloroglucitol), inositiol, should be mentioned, as well as the alcohols deriving from p-menthane, such as carvomenthol, menthol, $\alpha$ and $\gamma$-terpineol, 1-terpinenol, 4-terpinenol and piperitol, or the mixture of these alcohols as "terpineol", 1,4- and 1,8-terpin. Of the alcohols deriving from carbohydrates with condensed rings, for example those of the thujane, pinane or camphane group, useful also are thujanol, sabinol, pinol hydrate, D and L-borneol and D and L-isoborneol.

Aliphatic-cycloaliphatic polycyclic alcohols to be used for the esters are strerols, cholic acids and steroids, such as the sexual hormones and their synthetic analogues, and in particular corticosteroids and their derivatives. Thus it is possible to use for example: cholesterol, dihydrocholesterol, epidihydrocholesterol, coprostanol, epicoprostanol, sitosterol, stigmasterol, ergosterol, cholic acid, deoxycholic acid, lithocholic acid, estriol, estradiol, equilenin, equilin and their alkyl derivatives, as well as the ethynyl or propynyl derivatives in position 17, for example 17-$\alpha$-ethynyl-estradiol or 7-$\alpha$-methyl-17-$\alpha$-ethynyl-estradiol, pregnenolone, pregnanediol, testosterone and its derivatives, such as 17-$\alpha$-methyl-testosterone, 1,2-dehydrotestosterone and 17-$\alpha$-methyl-1,2-dehydrotestosterone, alkynyl derivatives in position 17 of testosterone and 1,2-dehydrotestosterone, such as 17-$\alpha$-ethynyltestosterone, 17-$\alpha$-propynyl-testosterone, norgestrel, hydroxyprogesterone, corticosterone, deoxycorticosterone, 19-nortestosterone, 19-nor-17-$\alpha$-methyltestosterone and 19-nor-17-$\alpha$-ethynyltestosterone, cortisone, hydrocortisone, prednisone, prednisolone, fludrocortisone, dexamethasone, betamethasone, paramethasone, flumethasone, fluocinolone, fluprednylidene, clobetasol, beclomethasone, aldosterone, desoxycorticosterone, alfaxalone, alfadolone, bolasterone.

Heterocyclic alcohols may be considered to be derivatives of the above-said cycloaliphatic or aliphatic-cycloaliphatic alcohols, if their linear or cyclic chains are interrupted by one or more, for example between one and three ethero atoms chosen from the group formed by —O—, —S—, —N and —NH and in these there may be one or more unsaturated bonds for example double bonds, particularly between one and three, thus including also heterocyclic compounds with aromatic structures. The following are specific useful examples: furfuryl alcohol, alkaloids and derivatives such as atropine, scopolamine, cinchonine, cinchonidina, quinine, morphine, codeine, nalorphine, N-butylscopolammonium bromide, ajmaline; phenylethylamines such as ephedrine, isoproterenol, epinephrine; phenothiazine drugs such as perphenazine, pipothiazine, carphenazine, homofenazine, acetophenazine, fluphenazine, N-hydroxyethylpromethazine chloride; thioxanthene drugs such as flupenthizol and clopenthixol; anticonvulsivants such as meprophendiol, antipsychotics such as opipramol; antiemetics such as oxypendil; analgesics such as carbetidine and phenoperideine and methadol; hypnotics such as etodroxizine; anorexics such as benzhydrol and diphemathoxidine; mild tranquilizers such as hydroxyzine; muscle relaxants such as cinnamedrine, diphylline, mephenesin, methocarbamol, chlorphenesin, 2,2-diethyl-1,3-propanediol, guaifenesin, idrocilamide; coronary vasodilators such as dipyridamole and oxyfedrine; adrenergic blockers such as propanolol, timolol, pindolol, bupranolol, atenolol, metoprolol, practolol; antieoplastics such as 6-azauridine, cytarabine, floxuridine; antibiotics such as chloramphenicol, thiamphenicol, erythromycin, oleandomycin, lincomycin; antivirals such as idoxuridine; peripheral vasodilators such as isonicotinyl alcohol; carbonic anhydrase inhibitors such as sulocarbilate; antiasthmatics and antiinflammatories such as tiaramide; sulfamides such as 2-p-sulfanylanilinoethanol.

3. Cross-Linked Hyaluronic Acid Derivatives

The invention may also use esters of polyhydric alcohols of hyaluronic acid resulting from the esterification of such alcohols with two or more carboxy groups of the hyaluronic acid polysaccharide, esters which, due to the presence of bridge bonds between the above carboxy functions of the same or different molecules of hyaluronic acid, may be described by the term "cross-linked". These cross-linked esters may be total or partial and, in the latter, further carboxy functions may be esterified with monohydric or polyhydric alcohols, without the formation of cross-links (ester groups which shall also hereinafter be termed "simple"). In both types of cross-linked partial esters, non-esterified carboxy functions may be free or salified with metals or organic bases.

The specific degree of cross-link esterification, that is the number of cross-linked groups of carboxy functions esterified with the above polyhydric alcohols, may be varied, this degree of esterification or salification being itself related to the solubility of the product and to its viscous-elastic properties. Thus, for example, the total cross-linked esters are virtually insoluble in aqueous liquids and are very suitable, due to their molecular structure, for use in the making of plastic materials and resins and as additives for these materials. Esters with an average or low degree of esterification and their salts with inorganic or organic bases are more or less soluble in aqueous conditions and are suitable for the preparation of gels.

The present invention may utilize total or partial cross-linked non-toxic esters of hyaluronic acid with an aliphatic polyhydric alcohol having between 2 and 16 carbon toms, and salts of such partial esters with inorganic or organic bases, wherein the cross-linking bonds are only between carboxy groups of the hyaluronic acid, with the proviso that said cross-linked ester is not the cross-linked ester of hyaluronic acid with a halomethyloxirane or a bisepoxy compound.

In the partial cross-linked esters, there may be carboxy groups esterified with monohydirc or polyhydric alcohols of the aliphatic, alicyclic, araliphatic or heterocyclic series, and in the partial esters there may be nonesterified, salified carboxy groups with inorganic or organic bases.

The cross-linked esters may derive from any polyhydric alcohol of an aliphatic nature, having between 2 and 16 carbon atoms, and these derive however preferably from polyhydric alcohols with a maximum of 8 alcohol functions and especially 4 such functions. The term "polyhydric", strictly speaking, generally refers to alcohols having three or more hydroxy groups, while the terms "dihydric" or "glycol" generally refer to alcohols having two hydroxy groups. However, as used herein the term "polyhydric" is meant to encompass alcohols having two or more hydroxy groups. Thus, the "polyhydric" alcohols may be dihydric alcohols, trihydric, tetrahydric, penta and hexahydric alcohols. Of these, special mention should be given to glycerine, the three erythrite isomers, pentaerythrite, the four xylitol isomers and the 10 dulcitol isomers.

In the esters the "cross-links" may derive from various of the above polyhydric alcohols, however it is preferable to prepare esters in which all the "cross-links" derive from the same polyhydric alcohol.

The most important class of the esters is the one deriving from dihydric alcohols, that is, from glycols. Such glycols have preferably a maximum of 8 carbon atoms, and are especially ethyleneglycol, propyleneglycol, butyleneglycol, the glycols deriving from pentane, hexane, heptane, octane and their position isomers. Such glycols may however also have double bonds, for example between one and three double bonds.

The simple ester groups, which may be present in addition to the cross-linked groups, may derive from alcohols of the aliphatic, araliphatic, alicyclic or heterocyclic series and may be substituted or unsubstituted, saturated or unsaturated. Alcohols of the aliphatic series are for example those with a maximum of 34 carbon atoms, which may be saturated or unsaturated and which may possibly also be substituted by other free functional or functionally modified groups, such as amino, hydroxy, aldehydro, keto, mercapto, carboxy groups or by groups deriving from these, such as hydrocarbyl or dihydrocarbylamino groups (here and hereafter the term "hydrocarbyl" should be taken to mean not only monovalent radicals of hydrocarbons e.g. of the $-C_nH_{2n+1}$ type, but also bivalent or trivalent radicals, such as "alkylenes"—$C_nH_{2n}$— or "alkylidenes"—$C_nH_{2n}$), ether or ester groups, acetal or ketal groups, thioether or thioester groups and esterified carboxy groups or carbamidic groups and substituted carbamidic groups by one or two hydrocarbyl groups, by nitrile groups or by halogens. Of the substituted alcohols it is preferable to choose those with one or two of the above-said functions.

Of the aforesaid groups containing hydrocarbyls, these are preferably lower aliphatic radicals, for example alkyls, with a maximum of 6 carbon atoms. Such alcohols may then also be interrupted in the carbon atom chain by heteroatoms, such as oxygen atoms, nitrogen, sulfur. Alcohols of the above group to be used preferentially are those with a maximum of 12 and especially 6 carbon atoms, and those, of the substituted ones, in which the hydrocarbyl radicals in the above said amino, ether, ester, thioether, thioester, acetal, ketal groups represent alkyl groups with a maximum of 4 carbon atoms, and in which in the esterified carboxy groups too, or substituted carbamidic groups, the hydrocarbyl groups are alkyls with the same number of carbon atoms, and in which the amino or carbamidic groups may be alkyleneamine or alkylene-carbamidic groups with a maximum of 8 carbon atoms. Of these alcohols, first and foremost should be mentioned those which are saturated and unsubstituted such as for example methyl, ethyl, propyl, isopropyl alcohols, n-butyl, isobutyl, tert-butyl alcohol, amyl alcohols, pentyl, hexyl, octyl, nonyl and dodecyl alcohols and above all those with a linear chain, such as n-octyl and n-dodecyl alcohols.

Of the substituted alcohols, preferred are the already mentioned glycols, otherwise used for the formation of "cross-links", but also polyhydric alcohols, such as glycerine, the aldehyde alcohols such as tartronic alcohol, carboxy alcohols such as lactic acids, for example .alpha.-oxypropionic acid, glycolic acid, malic acid, tartaric acids, citric acid, aminoalcohols, such as aminoethanol, aminopropanol, n-aminobutanol and their dimethyl and diethyl derivatives in the amino function, choline, pyrrolidinylethanol, piperidinylethanol, piperazinyl-ethanol and the corresponding derivatives of n-propyl alcohol or n-butyl alcohol, monothioethylenglycol or its alkyl derivatives, for example the ethyl derivative in the mercapto function. Of the saturate higher aliphatic alcohols, preferred are for example cetyl alcohol and myricyl alcohol, but of special importance for the aims of the present invention are the higher unsaturated alcohols with one or two double bonds, such as especially those contained in many essential oils and having an affinity with terpenes, such as for example citronellol, geraniol, nerol, nerolidol, linalool, farnesol and phytol. Of the unsaturated lower alcohols, allyl alcohol and propargyl alcohol are useful.

Of the araliphatic alcohols, preferred are all those with only one benzene residue and in which the aliphatic chain has a maximum of 4 carbon atoms and in which the benzene residue may be substituted by between 1 and 3 methyl or hydroxy groups or by halogen atoms, especially by chlorine, bromine or iodine, and in which the aliphatic chain may be substituted by one or more functions chosen from the group constituted by free amino or mono or dimethyl groups or by pyrrolidinyl or piperidinic groups. Of these alcohols, above all preferred are benzyl alcohol and phenethyl alcohol.

The alcohols of the cycloaliphatic series (including also cycloaliphatic-aliphatic alcohols) may derive from mono or polycyclic hydrocarbons and may have preferably a maximum of 34 carbon atoms. In the case of substituted alcohols, the substitutes may be those already mentioned for the alcohols of the aliphatic series.

Of the alcohols derived from monoannular cyclic hydrocarbons, preferred are those with a maximum of 12 carbon atoms, the rings having preferably between 5 and 7 carbon atoms, which may be substituted for example by between one and three lower alkyl groups, such as methyl, ethyl, propyl or isopropyl groups. As specific alcohols of this group preferred are cyclohexanol, cyclohexanediol, 1,2,3 cyclohexanetriol and 1,3,5 cyclohexanetriol (phloroglucitol), inositol. The heterocyclic alcohols may be considered as deriving from the above cycloaliphatic or aliphaticcycloaliphatic alcohols if in these the linear or cyclic chains are interrupted by one or more heteroatoms, for example between 1 and 3 heteroatoms chosen from the group formed by —O—, —S—, —N.dbd. and —NH— and in them there may be one or more double bonds, in particular between 1 and 3, thus including also heterocyclic compounds with aromatic structures. They may be simple alcohols, such as furfuryl alcohol or alcohols with a more complicated structure, such as are present in many alkaloid derivatives and in many medicaments.

The cross-linked derivatives may be prepared by methods per se known for the esterification of carboxy acids, for example by treatment of free hyaluronic acid with the above polyhydric alcohols in the presence of catalysts, such as strong inorganic acids or acid-type ionic exchangers, or with an etherifying agent able to introduce the desired alcohol residue in the presence of inorganic or organic bases. As etherifying agents it is possible to use those named in literature, such as especially the esters of various inorganic acids or organic sulfonic acids, such as hydrogen acids, that is the alkyl halogenide, such as methyl iodide or other alkyl groups which are at the base of the above bivalent alcohols.

The reaction may be effected in a suitable solvent, for example an alcohol, preferably the one corresponding to the alkyl group to be introduced into the carboxy group, but may also be effected in non-polar solvents such as ketones, ethers, such as dioxane or aprotic solvents, such as dimethylsulfoxide. As a base, it is possible to use for example a hydrate of an alkaline metal, alkaline earth metal or magnesium or oxide of silver or a basic salt of one of these metals, such as carbonate, and, of the organic bases, a tertiary azotized base, such as pyridine or collidine. Instead of the base, a basic-type ion exchanger may be used.

Another esterification method involves metal salts or salts with organic azotized bases, for example ammonium or ammonium substitute salts. Preferably, the salts of alkaline or alkaline earth metals should be used, but any other metal salt may also be used. The etherifying agents are also in this case those mentioned above and the same is true of the solvents. Preferably, aprotic solvents should be used, for example dimethylsulfoxide and dimethylformamide. These esterification methods may of course also be used to prepare the simple esters described above.

The method described in EP 0 265 116B1 can also be used to prepare the cross-linked esters. That is, the bridge bonds between two carboxy groups are easily formed by etherifying substances deriving from the above polyhydric alcohols on the quaternary ammonium salts of hyaluronic acid. As starting quaternary ammonium salts, it is preferable to use an inferior ammonium tetraalkylates, the alkyl groups having preferably between 1 and 6 carbon atoms. As a first choice, tetrabutylammonium hyaluronate should be used. These quaternary ammonium salts can be prepared by reacting a metal salt of hyaluronic acid, preferably one of those mentioned above, especially sodium or potassium salt, in aqueous solution with a sulfonic resin salified with the quaternary ammonium base. Tetraalkylammonium hyaluronate can be obtained by freeze-drying the eluate.

4. Hemiester of Succinic Acid or the Heavy Metal Salts of the Hemiester of Succinic Acid with Hyaluronic Acid Also useful in the present invention are the succinic hemiesters with hyaluronic acid or with a hyaluronic acid total or partial ester and its inorganic salt with a heavy metal as described in WO 96/35720.

In particular the succinic acid hemiester with hyaluronic acid, or with a hyaluronic acid total or partial ester is characterized by having the following repeating unit (I):

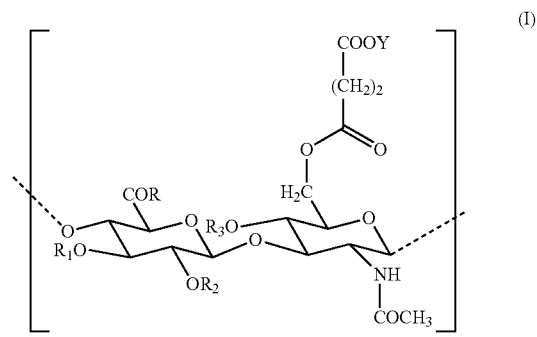

wherein $R_1$, $R_2$ and $R_3$ equal or different from each other are H or $CO(CH_2)_2COOY$, wherein Y is a negative charge or H, R is OH, O$^-$ or an alcoholic residue.

The hyaluronic acid esters contemplated for preparing the succinic acid hemiester are the total or partial ester with alcohol of the aliphatic or cycloaliphatic series, which do not themselves possess a notable pharmacological action disclosed in U.S. Pat. No. 4,851,521, which we incorporate herewith by reference.

The heavy metal salt of the succinic acid hemiester with hyaluronic acid or with a hyaluronic acid total or partial ester are in particular characterized by having the following repeating unit (II):

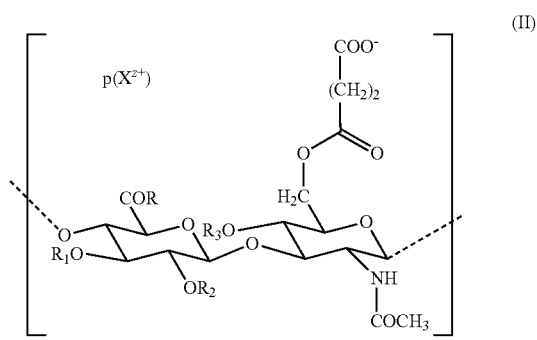

wherein $R_1$, $R_2$ and $R_3$ equal or different from each other are H or $CO(CH_2)_2COO^-$, R is O$^-$, or an alcoholic residue, ($X^{z+}$) is a cation of a heavy metal in which z is a number comprised between 1 and 6, p is an integer or a decimal number, comprised between 0.1 and 5 provided that $p(X^{z+})$ is equal to the number of anionic groups COO$^-$ present in said repeating unit. The heavy metal salts according to the present invention are characterized by having a far greater negative charge density than the corresponding heavy metal salt of the starting hyaluronate. Indeed, the substituting group, i.e. succinic acid, can bind, theoretically, to all the alcoholic functions of the repeating unit, giving a polysaccharide containing up to four succinic groups per repeating unit and therefore four more negative charges available for the formation of salts.

The term "heavy metal" encompasses any pharmaceutically active metal in the 4, 5 or 6 period of the periodic table. The preferred heavy metal salts are those whose cation is: zinc, silver, copper, gold, cerium and tungsten salts of succinic derivatives of hyaluronic acid.

It has in fact been found that compared with the corresponding salts with hyaluronic acid or with hyaluronic acid partial esters these salts offer an advantage over the already-known products containing heavy metal salts, because the salts according to the present invention can bind a high number of heavy metal cations. Indeed, while hyaluronic acid can bind only one counter-ion per repeating unit, the salts according to the present invention bind at least twice as many counter-ions per repeating unit.

Hyaluronic acid or hyaluronic acid esters of any molecular weight can be used to prepare succinyl derivatives thereof. Hyaluronic acid with a molecular weight of between 30,000 and 760,000 Daltons can be used, but this range is not critical for the purpose of the present invention.

Preferred succinic acid hemiesters of hyaluronic acid or hyaluronic acid esters are those having in the repeating unit (I) $R_1=R_2=R_3=H$ and the corresponding heavy metal salts wherein in the repeating unit (II) X is selected from the group consisting of: silver, gold, copper, zinc, z is comprised between 1 and 3 and p is comprised between 0.3 and 2.

Another class of preferred succinic acid hemiesters with hyaluronic acid or hyaluronic acid esters are those having at least one repeating unit (I) wherein $R_1=R_3=H$ and $R_2=CO-(CH_2)_2-COOY$ and at least one repeating unit (I), wherein $R_2=R_3=H$, and $R_1=CO-(CH_2)_2-COOY$ has the above mentioned meanings and the corresponding heavy metal salts have at least one repeating unit (II) wherein $R_1=R_3=H$ and $R_2=CO-(CH_2)_2-COO^-$ and at least one repeating unit (II) wherein $R_2=R_3=H$, $R_1=CO-(CH_2)_2-COO^-$, X is selected from the group consisting of: silver, gold, copper, zinc, z is comprised between 1 and 3 and p is comprised between 0.6 and 3.

5. O-Sulphated Derivatives of O/N-Sulphated Derivatives of Hyaluronic Acid

Also useful in the invention are hyaluronic acid derivatives which are

The term "partially 2-N-sulphated derivative" of hyaluronic acid as used herein means a product obtained by means of a controlled sulphation reaction of the amino group of the glucosamine of hyaluronic acid, previously N-deacetylated according to the procedure described by P. Shaklee (1984) Biochem. J. 217, 187-197. The reaction proceeds as illustrated below:

Diagram 1

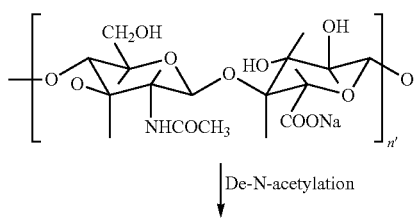

De-N-acetylation

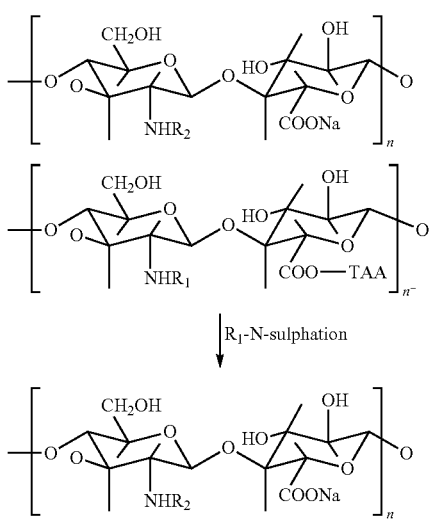

n: from 12 to 12500
$R_1$ = H, $COCH_3$
TAA = tetra-alkylammonium
$R_2 = SO_3, COCH_3$ The term "partially 2-N-sulphated and 6-O sulphated derivatives" as used herein means the products of the chemical reaction illustrated in diagram 1, wherein, besides the amino group of glucosamine, the primary hydroxy function of the same residue is also totally or partially involved in the sulphation reaction, as illustrated below:

Diagram 2

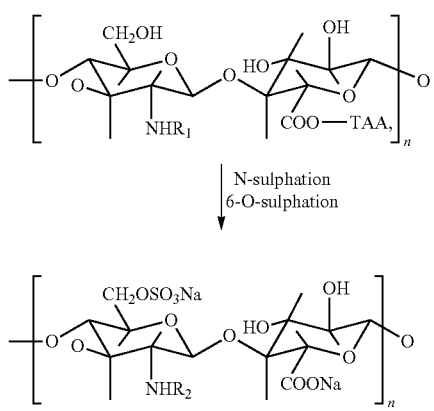

n: from 12 to 12500
$R_1$ = H, $COCH_3$
TAA = tetra-alkylammonium
$R_2 = SO_3, COCH_3$ The derivatives generated according to diagrams 1 and 2 can also be used as intermediate reactants in the preparation of compounds, according to the procedure described in European patent 0216453 B1, wherein the carboxy function of the glucuronic residue of hyaluronic acid, partially 2-N-sulphated or partially 2-N-sulphated and partially or totally 6-O-sulphated, is partially or completely reacted with alcohols of the aliphatic, aromatic, arylaliphatic, cycloaliphatic, heterocyclic series, producing the respective partial or total esters:

Diagram 3

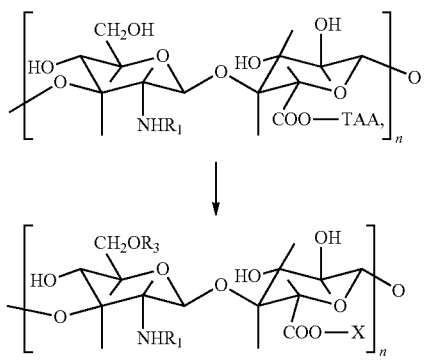

n: from 12 to 12500
$R_1$ = H, COCH$_3$
TAA = tetra-alkylammonium
$R_2$ = SO$_3$, COCH$_3$
$R_3$ = SO$_3$, H
X = alcoholic residue, Sodium Moreover, it is possible to use the synthetic derivatives according to diagrams 1 and 2 as intermediates in the preparation of crosslinked compounds, according to the procedures described in European patents 0341745 B1 and 265116 B1 respectively, wherein a part or all of the carboxy groups belonging to the D-glucuronic residue are reacted: i) using condensing agents with the alcohol functions of the same polysaccharide chain or other chains, generating inner (or lactone) esters and intermolecular esters; ii) with poly-alcohols of the aliphatic, aromatic, arylaliphatic, cycloaliphatic, heterocyclic series, generating crosslinking by means of spacer chains.

The above-said sulphated compounds obtained according to the process described in PCT/EP98/01973 can be optionally salified with heavy metals, the heavy metals being selected from the group of metal elements in the $4^{th}$ $5^{th}$ and $6^{th}$ periods of the periodical table, such as silver, iron, cobalt, copper, zinc, arsenic, strontium, zirconium, antimonium, gold, cesium, tungsten, selenium, platinum, ruthenium, bismuth, tin, titanium, and mercury.

Lastly, the sulphated derivatives can be optionally salified with pharmacologically active substances such as antibiotics, anti-infective, antimicrobial, antiviral, cytostatic, antitumoral, anti-inflammatory and would healing agents, anesthetics, cholinergic or adrenergic agonists or antagonists, antithrombotic, anticoagulant, haemostatic, fibrinolytic and thrombolytic agents, proteins and their fragments, peptides, and polynucleotides.

Of the hyaluronic acid esters, the ones with between 65% and 80% esterification are especially preferred.

The hyaluronic acid derivatives can be prepared in various forms such as gels, guide channels, sponges, non-woven fabrics, threadsy, unperforated or perforated membranes, microspheres nanospheres, gauze pads and their associations, optionally together with one or more additional pharmaceutically acceptable carrier or excipient.

The compositions of the present invention may also contain pharmacologically or biologically active substances such as antibiotics, growth factors, antimicotic, antimicrobial, antiviral agents, disinfectants, anaesthetics, and phospholipids. Said active substances may also be vehicled and released using hyaluronic acid and its derivatives in the form of microspheres and nanospheres and also in the form of the previously described biomaterials.

Example 1

Decrease in the area of cutaneous scarring in a rat model following treatment of the wound with the benzyl ester of hyaluronic acid (HYAFF® 11) with 75% esterification and hyaluronic acid/Hyalastine® fraction).

The animals were sedated by intramuscular injection of ketamine/xilazine (0.1 mg/g or 2.5 ml of solution). Anesthesia by the inhalation of metophane was also performed and the breathing rate was monitored to ensure sufficient ventilation. The backs of the animals wee shaved, washed and disinfected with chlorhexidine and iodate solution.

A maximum of four full-thickness wounds were performed on each animal, using a punch with a 6-mm diameter.

The wounds were treated as described in Table 1:

| Groups | Number of treated sites | Treatment |
|---|---|---|
| 1 | 18 | Partial benzyl ester of hyaluronic acid HYAFF ® 11p 75% in the form of a non-woven fabric |
| 2 | 18 | Hyaluronic acid (60 mg/ml) | hyaluronic acid Hyalastine ® fraction (EP 0 138 572 B1)
HYAFF ® 11p 75% in the form of a nonwoven fabric (U.S. Pat. Nos. 4,851,521; 4,965,353)

Two of the wounds in each animal were treated, and two were used as control, so as to have inside control for site. The treated areas (3 per treatment group) were removed at set times (1, 3, 7, 14, 28, 42 days). The specimens were cut into sections and stained with Mallory's triple stain. The sections were analyzed by optical microscope and the scarred area was measured. Graph 1 reports value expressed as percentages of scar area of the treated sites compared to that of the untreated sites, and each value corresponds to the mean of three determinations on three different animals.

It is evident that a single application of the partial benzyl ester of hyaluronic acid (HYAFF®p75%) is better able to prevent the formation of scarring than a single application of hyaluronic acid (60 mg/ml). Indeed, as early as the $14^{th}$ day, it is possible to observe that the scarred areas of the group treated with HYAFF®p75% are 40% less extensive than the control areas, while in the case of the sites treated with hyaluronic acid the scarred areas are more extensive than the control areas.

Each of the publications referred to herein are hereby expressly incorporated by reference.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims:

The invention claimed is:

1. A method for the treatment of cutaneous scarring on the skin which comprises applying to the treatment area an effective amount of a pharmaceutical composition in the form of a non-woven fabric comprising a 75% benzyl ester of hyaluronic acid, wherein 75% of the carboxylic group of hyaluronic acid are benzyl esterified, and the remaining carboxylic groups are free or salified wherein said extent of scarring is reduced by at least 40% compared to areas treated with hyaluronic acid.

2. The method according to claim 1, wherein said treatment results in reduced normotrophic scarring.

3. The method according to claim 1, wherein or biologically active substance selected from the group consisting of an antibiotic, growth factor, antimicotic, antimicrobial, antiviral agent, disinfectant, phospholipid and anaesthetic.

4. The method according to claim 1, wherein the hyaluronic acid derivative is a benzyl ester of hyaluronic acid wherein 75% of the carboxy functions are esterified with benzyl alcohol and the remaining carboxylic groups of hyaluronic acid are salified to form an inorganic salt.

5. The method according to claim 1, wherein said inorganic salt is a salt with an alkaline or alkaline earth metal.

6. The method according to claim 5, wherein said salt is a salt with potassium, sodium and ammonium.

7. The method according to claim 1 which comprises a single application of said 75% benzyl ester of hyaluronic acid to said skin.

* * * * *

UNITED STATES PATENT AND TRADEMARK OFFICE
CERTIFICATE OF CORRECTION

PATENT NO. : 8,147,811 B1
APPLICATION NO. : 10/019387
DATED : April 3, 2012
INVENTOR(S) : Maurizio Dalle Carbonare et al.

It is certified that error appears in the above-identified patent and that said Letters Patent is hereby corrected as shown below:

In the claims:

At column 19, claim number 3, line number 6, should read:

-- 3. The method according to claim 1, wherein <u>said benzyl ester of hyaluronic acid is applied in association with at least one additional pharmacologically</u> or biologically active substance selected from the group consisting of an antibiotic, growth factor, antimicotic, antimicrobial, anti-viral agent, disinfectant, phospholipid and anaesthetic. --

At column 19, claim number 4, line number 10, should read:

-- 4. The method according to claim 1, wherein <u>said</u> ~~the hyaluronic acid derivative is a benzyl ester of hyaluronic acid wherein 75% of the carboxy functions are esterified with benzyl alcohol and the~~ remaining carboxylic groups of hyaluronic acid are salified to form an inorganic salt. --

At column 20, claim number 5, line number 3, should read:

-- 5. The method according to claim 1, wherein said <u>salified carboxylic groups are salified to form an</u> inorganic salt <u>which</u> is a salt with an alkaline or alkaline earth metal. --

Signed and Sealed this
Thirteenth Day of August, 2013

Teresa Stanek Rea
*Acting Director of the United States Patent and Trademark Office*